United States Patent [19]
Bokros et al.

[11] Patent Number: 5,545,216
[45] Date of Patent: Aug. 13, 1996

[54] PROSTHETIC HEART VALVE

[75] Inventors: Jack C. Bokros; John L. Ely; Michael R. Emken, all of Austin; Axel D. Haubold, Liberty Hill; T. Scott Peters, Georgetown; Jonathan C. Stupka, Austin; C. Thomas Waits, Pflugerville, all of Tex.

[73] Assignee: Medical Carbon Research Institute, LLC, Austin, Tex.

[21] Appl. No.: 441,791

[22] Filed: May 16, 1995

[51] Int. Cl.$^6$ .................................................. A61F 2/24
[52] U.S. Cl. .................................................. 623/2
[58] Field of Search ................................. 623/2, 900

[56] References Cited

U.S. PATENT DOCUMENTS

| | | | |
|---|---|---|---|
| 4,451,937 | 6/1984 | Klawitter . | |
| 4,689,046 | 8/1987 | Bokros | 623/2 |
| 5,116,367 | 5/1992 | Hwang et al. | 623/2 |
| 5,123,920 | 6/1992 | Bokros | 623/2 |
| 5,137,532 | 8/1992 | Bokros et al. | 623/2 |
| 5,152,785 | 10/1992 | Bokros et al. | 623/2 |
| 5,192,309 | 3/1993 | Stupka et al. | 623/2 |
| 5,314,467 | 5/1994 | Shu | 623/2 |
| 5,326,372 | 7/1994 | Mhatre et al. | 623/2 |
| 5,350,421 | 9/1994 | Stupka et al. | 623/2 |
| 5,376,111 | 12/1994 | Bokros et al. | 623/2 |

FOREIGN PATENT DOCUMENTS

8802247  4/1988  WIPO ........................... 623/2

*Primary Examiner*—David H. Willse
*Attorney, Agent, or Firm*—Fitch, Even, Tabin & Flannery

[57] ABSTRACT

A bileaflet heart valve is shown which incorporates a pivot arrangement that minimizes resistance to downstream blood flow in the open position yet has prompt response and therefore minimal regurgitation upon flow reversal. The valve employs a pair of identical flat leaflets that can assume a precisely parallel orientation in the fully open position at or near peak downstream blood flow or can alternatively assume other low energy positions. As the downstream flow of blood slows near the end of a pumping stroke, downstream displacement of the leaflets results in their prerotation toward the closed position orientation, all being controlled by the interengagement of flat ears, which extend laterally from opposite surfaces of the leaflets, and receiving cavities of unique design. The cavities include upstream and downstream lobes separated by an intermediate throat portion defined by inward and outward fulcrums. As soon as reverse flow begins, upstream displacement of the leaflets causes the ears to contact straight camming surfaces located upstream of the outward fulcrums which, in combination with the fulcrums and a downwardly directed, concave surface at the upstream end of the upstream lobe, positively guide each leaflet through efficient closing which ends in substantially rotational movement.

19 Claims, 10 Drawing Sheets

PROSTHETIC HEART VALVE

FIELD OF THE INVENTION

The present invention relates to mechanical heart valve prostheses and, in particular, to improved prosthetic heart valves having pairs of valve members or occluders which both pivot and translate in moving between their open and closed positions.

BACKGROUND OF THE INVENTION

A wide variety of heart valve prostheses have been developed which operate hemodynamically, in conjunction with the pumping action of the heart, to take the place of a defective natural valve. These valves have generally been designed to function with valve members in the form of a single occluder, a pair of occluders or leaflets or even three or more occluders; such occluders pivot along eccentric axes (or both pivot and translate) to open and close a central blood flow passageway through a generally annular valve body within which the occluders are usually appropriately supported.

U.S. Pat. No. 4,451,937 (Jun. 5, 1984) discloses an early heart valve design wherein arcuate depressions in flat sidewall sections of a valve body guide valve members having ears extending from their lateral edges that are received in such depressions.

U.S. Pat. No. 4,689,046 (Aug. 25, 1987) discloses a bileaflet heart valve having a pair of flat leaflets with ears of generally trapezoidal configuration extending from the flat lateral surfaces thereof. The ears have flat end faces and are received in diametrically opposed recesses in the valve body having facing flat end surfaces; the recesses are shaped so that the ears are rockingly engaged therein by tapered recess guide wall surfaces of arcuate configuration.

U.S. Pat. No. 5,123,920 (Jun. 23, 1992) discloses a bileaflet heart valve having curved leaflets with bulbous downstream sections having a pivot construction wherein notches are formed in the outflow surfaces of thickened portions of the pair of leaflets, which notches engage complementary surfaces on pivot projections that extend radially inward from diametrically opposite locations on the valve body sidewall.

U.S. Pat. No. 5,137,532 (Aug. 11, 1992) discloses bileaflet heart valves having pivot arrangements which allow the leaflets to assume an orientation substantially parallel to the centerline through the valve in their open position in a valve body which is elongated in axial length relative to bileaflet valves of earlier design wherein designers generally attempted to minimize the length of the blood flow path through the valve body, because the valve was felt to be confining. In one embodiment, camming surfaces provided on the leaflets engage appropriately located projections extending radially inward from the valve body sidewall, and the upstream displacement of the leaflets which occurs upon the reversal of blood flow causes prompt pivoting of the leaflets toward the closed positions.

U.S. Pat. Nos. 5,152,785 (Oct. 6, 1992) and No. 5,192,309 (Mar. 9, 1993) show heart valves which are generally similar to that last mentioned. The '309 patent illustrates valves having an alternative construction wherein inclined camming surfaces are provided on projections located at the upstream edge of the valve body, which are engaged by the upstream edges of the respective leaflets to create a camming action. Guidance for determining the path of the leaflets is also provided by cylindrical lateral ears that translate in slots formed in flat sidewall portions of the valve body.

U.S. Pat. No. 5,350,421 (Sep. 27, 1994) is similar to the '309 patent and specifically illustrates a construction that is responsible for prerotation of the leaflets occurring at the end of the downstream flow of blood through the valve just prior to its reversal.

U.S. Pat. No. 5,314,467 (May 24, 1994) discloses a bileaflet heart valve wherein leaflets of composite curvature are supported by laterally extending elongated ears which are received in recesses formed in diametrically opposed flat wall sections of the interior surface of a valve body that is formed with a flared outflow seat region against which the leaflet downstream edges seat. The recesses each have a serpentine guide wall along the upstream edge thereof. The combination of it and a second downstream wall creates a sequence of rotational and then translational movement of the leaflets as they pivot from the open position to the closed position.

Although heart valves have been developed and are currently in use incorporating various of the features of the above-mentioned U.S. patents, the search continues for improved mechanical heart valve prostheses that provide passageways through which blood will flow freely and with a minimum of drag in the open position, which will close quickly upon the occurrence of backflow to minimize regurgitation of blood, and which can be efficiently manufactured and assembled. Accordingly, new valve designs incorporating such features have continued to be sought.

SUMMARY OF THE INVENTION

The present invention provides bileaflet mechanical heart valve prostheses having the aforementioned desirable characteristics wherein leaflets can assume an orientation in the open position where they are parallel to the longitudinal axis of the valve passageway but will still promptly close, with guidance and control of the leaflets being accomplished solely by contact between laterally protruding ears and complementary-shaped cavities in the sidewalls of the valve body in which they are received which have straight camming edges that are angularly located to achieve prompt pivoting, thus easing manufacturing requirements because the most critical tolerances to be maintained are substantially confined to a single region of the valve body. Moreover, although the leaflets may be parallel when blood flow is at its highest level yet, when the velocity of the downstream blood flow slows near the end of the pumping stroke, they undergo a prerotation toward their closed orientation from such parallel orientation. As a result of such prerotation and the design of the pivot arrangement, closing of the valve occurs even more promptly and with a minimum of regurgitation and with final movement that is substantially purely rotational. The leaflets preferably have rectilinear surfaces that will assume an orientation in alignment with the instantaneous direction of blood flow in the full open position, e.g. precisely parallel to the centerline through the valve, thereby minimizing resistance to the downstream flow of blood; such rectilinear leaflet surfaces can be flat or cylindrical.

DETAILED DESCRIPTION OF THE PREFERRED EMBODIMENTS

Figure 1:
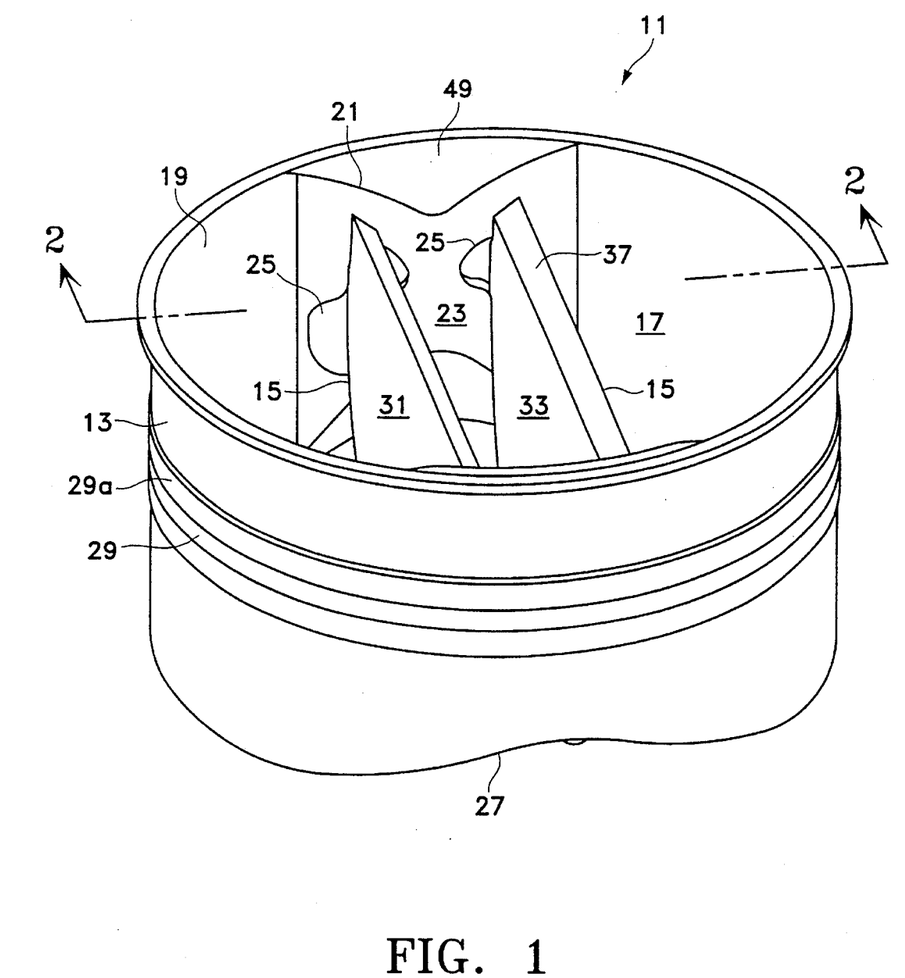
FIG. 1 is a perspective view of a bileaflet heart valve embodying various features of the present invention, shown with the leaflets in the open position.

Illustrated in FIG. 1 is a preferred embodiment of a prosthetic heart valve 11 constructed so as to embody various features of the present invention. Very generally, heart valves having this construction have improved flow characteristics, particularly when the valve is in its fully open position, because the leaflets can align parallel to the valve centerline or can align at slight deviations thereto depending upon instantaneous variations in the blood flow path through the valve at any instant, whichever is the low energy orientation. As a result, these orientations minimize the resistance to blood flow and substantially reduce boundary layer separation along major surfaces of the leaflets. The valve design also provides good washing characteristics which guard against the occurrence of stagnation and potential clotting. Importantly, although heart valves of this design exhibit a rapid response to change in the direction of blood, both in respect of opening and closing, the final movement of the closing leaflets is one almost solely of rotation so that there is relatively low wear due to the leaflet rubbing against a fulcrum within the valve body at about the time of complete closing, thus eliminating potential problems which could result from the creation of regions of substantial wear on the leaflet and on the fulcrum by translation movement during the final closing phase when the pressure across the valve is building to the maximum value.

Figure 2:
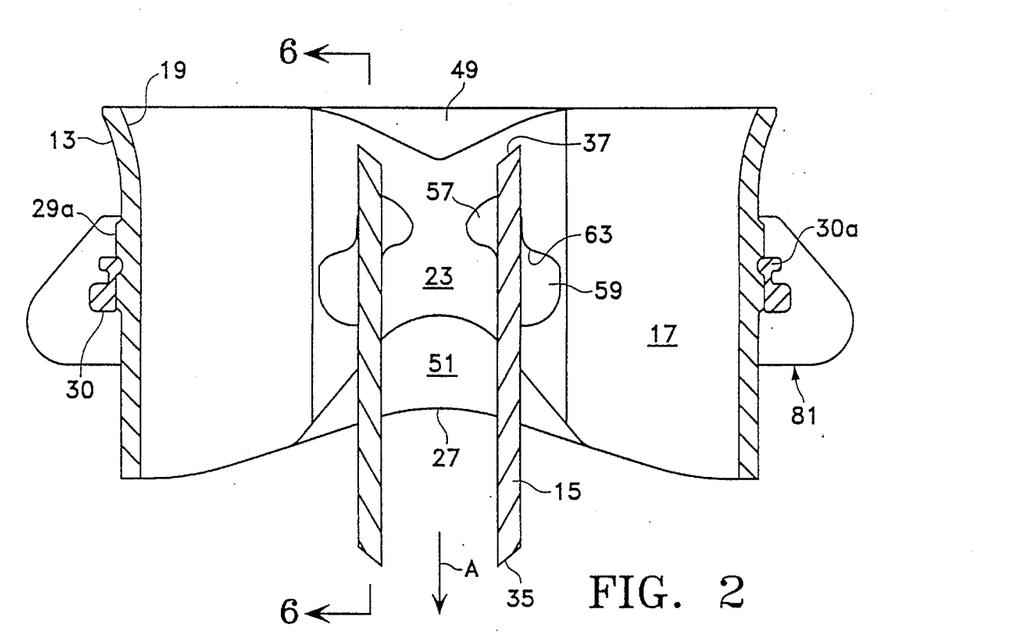
FIG. 2 is a sectional view taken generally along the line 2—2 of FIG. 1 showing the leaflets in the full open position, and with a suture ring attached to the valve body.

Heart valve 11 includes a generally annular valve body 13 which carries a pair of pivoting occluders or leaflets 15 that alternately open and close either to allow the smooth flow of blood in the downstream direction, as indicated by the arrow A in FIG. 2, or to prevent any substantial backflow of blood, i.e. regurgitation. The valve body 13 defines a blood flow passageway in the form of its generally arcuate, mostly cylindrical interior wall surface 17. The valve body 13 has a curved entrance region 19 at its upstream end, which has been found to substantially increase streamlined flow characteristics through the valve. It also has a pair of diametrically opposed, thickened wall sections 21 that terminate in interior flat wall surfaces 23 in which pairs of cavities or recesses 25 are formed that function as a part of the pivot arrangement for defining the opening and closing movements of the leaflets 15.

The valve body 13 preferably has a scalloped downstream profile so that there are, in effect, a pair of shallow notches 27 formed in the contour of the valve body 13 in the regions just downstream of the thickened wall sections 21. In a bileaflet valve of this type, the side openings provided by these notches 27 are aligned with the central passageway between the leaflets 15 so that, upon reversal of blood flow, backflowing blood laterally enters the valve body through these side openings directing a surge of blood flow into the central passageway region and creating forces which impinge upon the leaflet outflow surfaces, the effect of which is to further enhance prompt pivoting of the eccentrically mounted leaflets toward their closed position orientations. This function is described in greater detail in U.S. Pat. No. 5,308,361, the disclosure of which is incorporated herein by reference.

The exterior surface of the valve body 13 is provided with a slightly thickened central portion 29a that includes a shallow groove 29 of arcuate cross section which is designed to receive a metal stiffening ring 30 of irregular shape that adds stability and rigidity to the valve body. The valve body itself is preferably made of a material having some resiliency, such as pyrocarbon or pyrocarbon-coated graphite as is well known in this art, which can be deformed so as to permit the assembly of the pair of leaflets 15 into their operative locations. The metal stiffening ring 30 is used to support a sewing or suture ring of an appropriate design. Detailed examples of sewing rings which can be employed are described in U.S. Pat. Nos. 4,535,483 and 3,691,567. Two such sewing ring designs are discussed hereinafter in general detail.

The leaflets 15 are preferably identical in shape and size. Each leaflet has two rectilinear, preferably flat, surfaces, i.e. an inflow surface 31 and an outflow surface 33, and the leaflet is preferably of substantially constant thickness such that the surfaces 31 and 33 are parallel to each other. The inflow surface 31 is arbitrarily defined as the surface which faces upstream with the leaflets in the closed position (see FIG. 4), whereas the outflow surface 33 faces downstream. Although the leaflets 15 are preferably flat, other configurations, such as sections of hollow cylinders of circular or elliptical cross section, can alternatively be employed, as discussed in more detail in U.S. Pat. No. 5,246,453, the disclosure of which is incorporated herein by reference.

Figure 4:
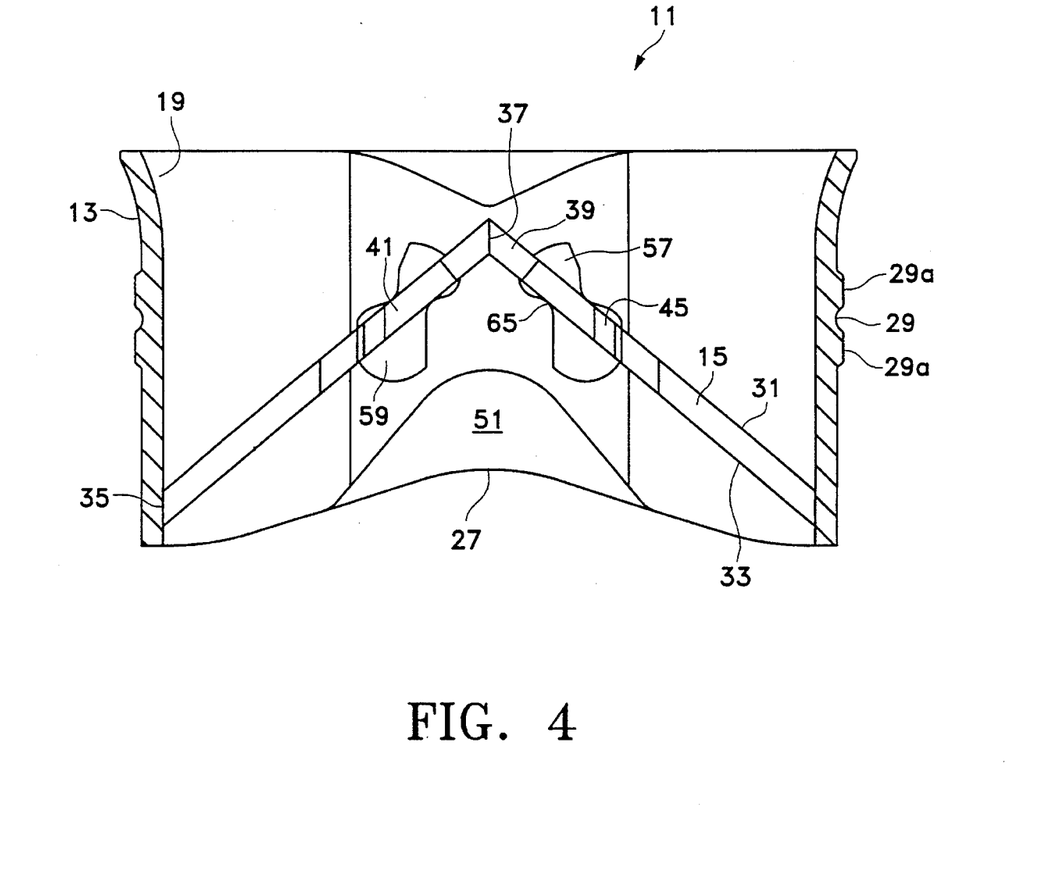
FIG. 4 is a view similar to FIG. 2, showing the leaflets in elevation and in their closed position, with the suture ring omitted.

The leaflets 15 each have a major arcuate edge surface 35, which is located at the downstream edge of the leaflet in the open position, and each has a minor mating edge surface 37 which is located at the opposite, upstream edge of the leaflet in the open position. The arcuate edge surface 35 preferably has a configuration such as to abut and seat closely against the cylindrical sidewall interior surface 17 of the valve body in the closed position. The minor edge surface 37 is preferably flat and formed at an angle so as to mate flush against the corresponding mating edge surface 37 of the opposing leaflet in the closed position, as best seen in FIG. 4. As a result, the minor edge surface 37 is accordingly oriented at an angle to the inflow surface 31 which is substantially the same as the downstream angle which the outflow surface 33 forms with the centerline plane in the closed position, and it is preferably an angle between about 30° and about 60°. The centerline plane is defined as a plane which includes the centerline of the passageway and which is parallel to the pivot axes of the leaflets; in the illustrated embodiment, it is perpendicular to the flat wall surfaces 23 of the valve body passageway. The angle in question defines the extent of the angular rotation that each leaflet 15 will undergo in moving from the fully open position to the fully closed position. This is taken into consideration because there may be an advantage in having a smaller angle, as opposed to a larger angle, because the leaflets need not rotate as great an angular distance in order to reach the fully closed position. As illustrated in FIG. 4, this angle is about 50° in the preferred embodiment.

Figure 7:
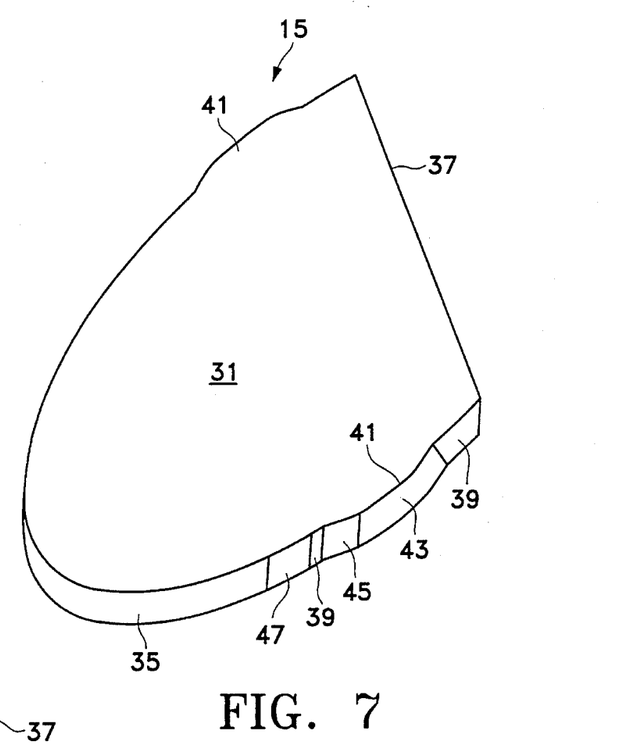
FIG. 7 is a perspective view of a leaflet from the valve of FIG. 1.
Figure 8:
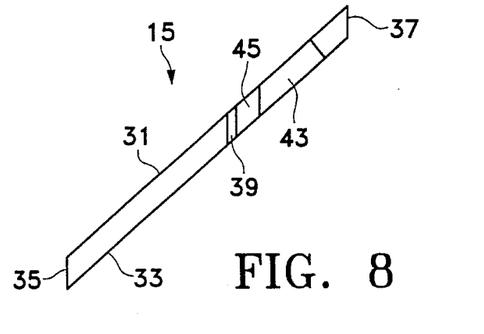
FIG. 8 is a side elevation view, reduced in size, of the leaflet of FIG. 7.
Figure 9:
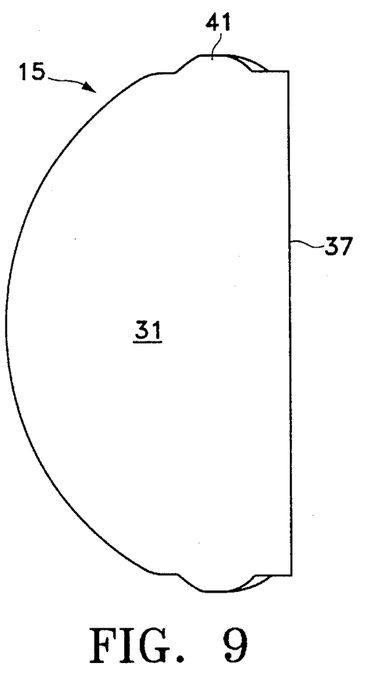
FIG. 9 is a front view of the leaflet of FIG. 8.

As best seen in FIG. 7, the leaflets 15 each have a pair of intermediate straight edge regions 39 located between the minor mating edge surface 37 and the major arcuate edge surface 35 wherein a pair of laterally extending ears or tabs 41 are located. As can be seen in FIG. 8, the ears 41 are the same thickness as the flat leaflets 15 from which they laterally extend. The ears 41 are elongated in an upstream-downstream direction when viewed in their open orientation. FIGS. 7 and 9 show that the ears 41 have lateral edge surfaces which are rectilinear surfaces of generally shallow curvature as viewed looking at the leaflet from the inflow surface 31. More specifically, as best seen in FIG. 7, they each have a shallow rounded upstream edge surface 43 and downstream edge surface 45. The two lateral edge surfaces 43 and 45 of the ears meet and blend smoothly into each other. The major portion of the upstream edge rectilinear surface 43 is perpendicular to the flat inflow and outflow surfaces of the leaflets 15, which flat surfaces simply extend through the regions of the ears, so that the ears have inflow and outflow surfaces that are coplanar with the leaflet main body inflow and outflow surfaces 31, 33. A short arcuate transition edge section 47 is interposed between the major arcuate edge surface 35 and the flat section 39.

As previously mentioned, the valve body 13 is formed with the thickened wall sections 21 in the regions where the cavities 25 are located, and preferably these thickened sections are formed with flaring transition surfaces, i.e. an upstream transition surface 49 and a downstream transition surface 51 which lead smoothly from the circular entrance region and the circular exit region of the valve body to the flat wall surfaces 23 wherein the cavities 25 are located. A surface such as the surface 49 may be referred to as a radial swept surface. As a result, the flow passageway through the valve body is generally circular in cross-section except for the two thickened sections 21 which extend inward to the flat wall surfaces 23. As previously indicated, the plane containing the centerline axis of the generally circular passageway that is oriented perpendicular to the flat surfaces 23 is referred to as the centerline plane and is frequently used for reference purposes throughout this specification.

Figure 12:
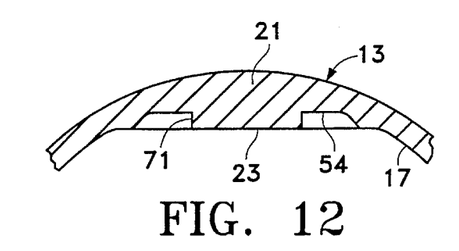
Figure 13:
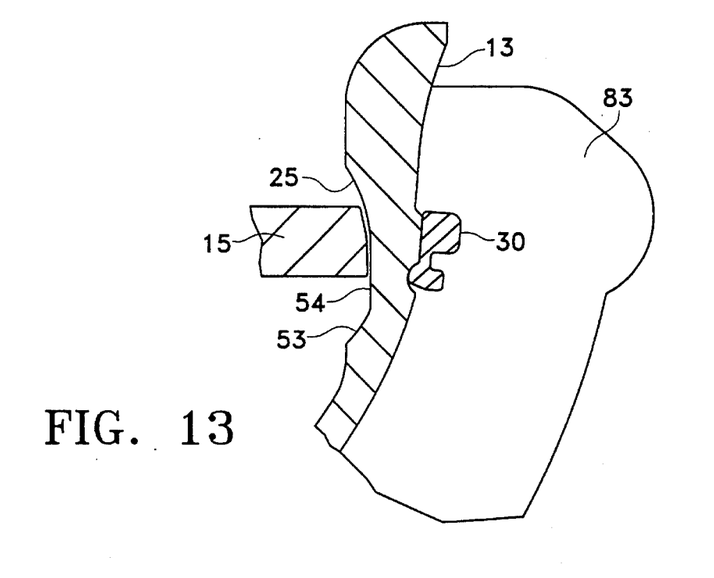
FIG. 13 is a fragmentary sectional view taken generally along the line 13—13 of FIG. 2A.

The arrangement is such that each thickened section includes two side-by-side cavities which are mirror images of each other and which are located on opposite sides of this centerline plane. As seen in FIGS. 12 and 13, the cavities 25 each have a curved sidewall region 53 surrounding a central flat rear section 54; however, the depth of the cavities 25 is such that the apex of the curved upstream edge surface 43 of the ear does not quite touch the rear walls 54 of the cavities, e.g. a clearance of about 1–4 mils (0.001–0.004 inch). The flat wall surfaces 23 of the thickened regions serve as the primary bearing surfaces against which one or the other of the straight edge surfaces 39 of the leaflets will usually bear whenever the leaflet is moving between its open and the closed positions. The clearance between the shallow curved edge surface 43 of the ear and the rear wall of the cavity is such to facilitate a controlled cleansing spurt of blood flow, upstream through the cavity past the leaflet ears during the moment of complete closure of the valve as shown in FIG. 4; this guards against the possibility of the occurrence of clotting in the pivot region. The proportioning of the ears 41 and the cavities is such that this cleaning leak is not a high velocity jet that might cause hemolysis; instead, it is a controlled flow through a long narrow leak path that does not induce thrombosis.

Figure 10:
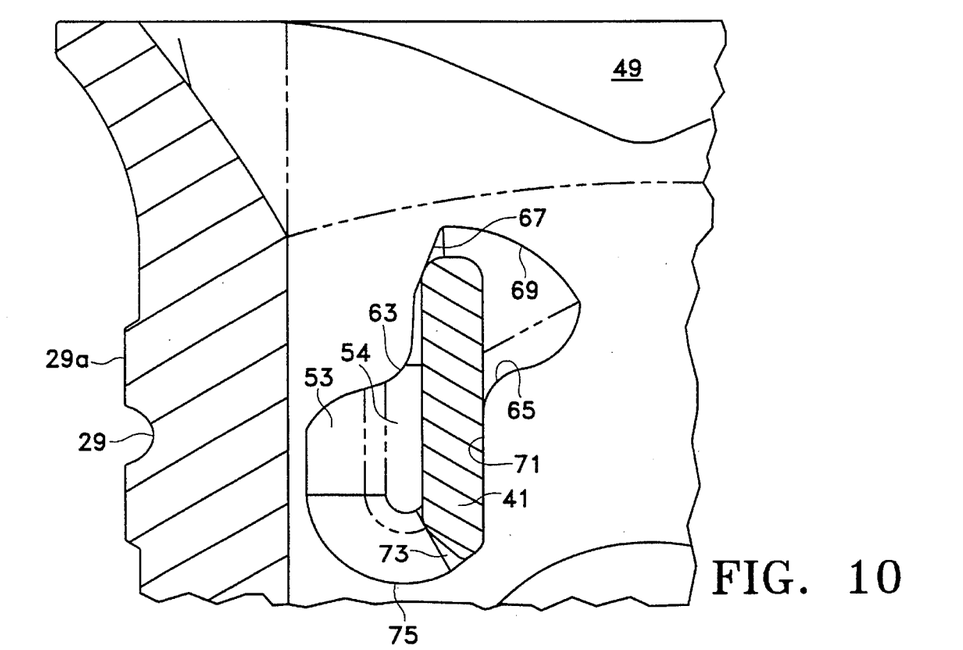
FIG. 10 is a fragmentary sectional view, enlarged in size, taken generally along the line 10—10 of FIGS. 5 and 6, showing the location of the ear in the cavity in the valve body sidewall when the leaflet is in its full open position.

As best seen perhaps in FIG. 10, the cavities 25 are formed to have an upstream lobe 57 and a downstream lobe 59 on opposite sides of an intermediate throat section 61. The intermediate throat section is formed by a pair of curved fulcrums termed an outward fulcrum 63 and an inward fulcrum 65 with respect to their location having reference to the centerline plane. The outward fulcrum 63 is located substantially even with, but preferably slightly upstream of said inward fulcrum.

The upstream lobe 57 is formed with an inclined, straight, camming wall section 67, which is oriented at an angle of between about 5° and about 30° to the centerline plane and preferably between about 15° and about 25°. Although the camming wall section 67 is part of the peripheral wall region 53 and thus has curvature in a radial direction, it is substantially rectilinear and is thus referred to as being straight. At its upstream end, the camming wall section joins a concavely curved wall section 69, which leads gradually downstream from this junction point and serves a guidance function that is described hereinafter.

The downstream lobe 59 includes a flat locating wall section 71 immediately below the inward fulcrum, at the downstream end of which wall there is a downstream sloping section 73 leading from its junction point to the downstream end 75 of the cavity. The flat wall section 71 is oriented parallel to the centerline plane and thus provides a guide surface against which the outflow surfaces of the ears 41 bear in the full open position, as best seen in FIGS. 2 and 9. As best seen in FIG. 8, the leaflet ears 41 preferably have their rounded downstream edge surfaces 45 oriented so as to be at an acute angle to the outflow surface 33 of the leaflet, thus presenting essentially a line of contact between the ear downstream edge surface 45 and the sloping wall section 73, which tends to reduce friction and promote cleansing in this region.

The leaflets 15 are installed in the valve body 13 by squeezing the body at diametrically opposite locations, as for example along a diameter which is perpendicular to the centerline plane. Such deformation of the heart valve body 13 can take place in accordance with the teachings of U.S.

Pat. No. 5,336,259, issued Aug. 9, 1994, the disclosure of which is incorporated herein by reference. Squeezing causes the diametrically opposed flat wall sections 23 to separate farther from each other to permit the leaflets to be fitted into the valve body, with the ears 41 being received in the cavities 25. When the squeezing force is removed, the valve body 13 returns to its original annular configuration, leaving only the desired minimal clearance between the flat wall surfaces 23 of the valve body and the straight lateral edge surfaces 39 of the leaflets, in which positions the leaflets are slidably-pivotally mounted for travel between the open and closed positions. The metal stabilizing ring 30 can be appropriately installed, as by snapping into place or by shrink-fitting, in the exterior circumferential groove 29 following the installation of the leaflets; however, it may be preferred to install the metal stabilizing ring before installing the leaflets. Pyrocarbon is the preferred material of valve body construction, and compressive force applied to a pyrocarbon structure by such a metal ring can improve the structural properties of a pyrocarbon valve body. Such a metal ring will be chosen which will have sufficient resiliency to return to its perfectly annular shape following removal of such a squeezing force.

Figure 6:
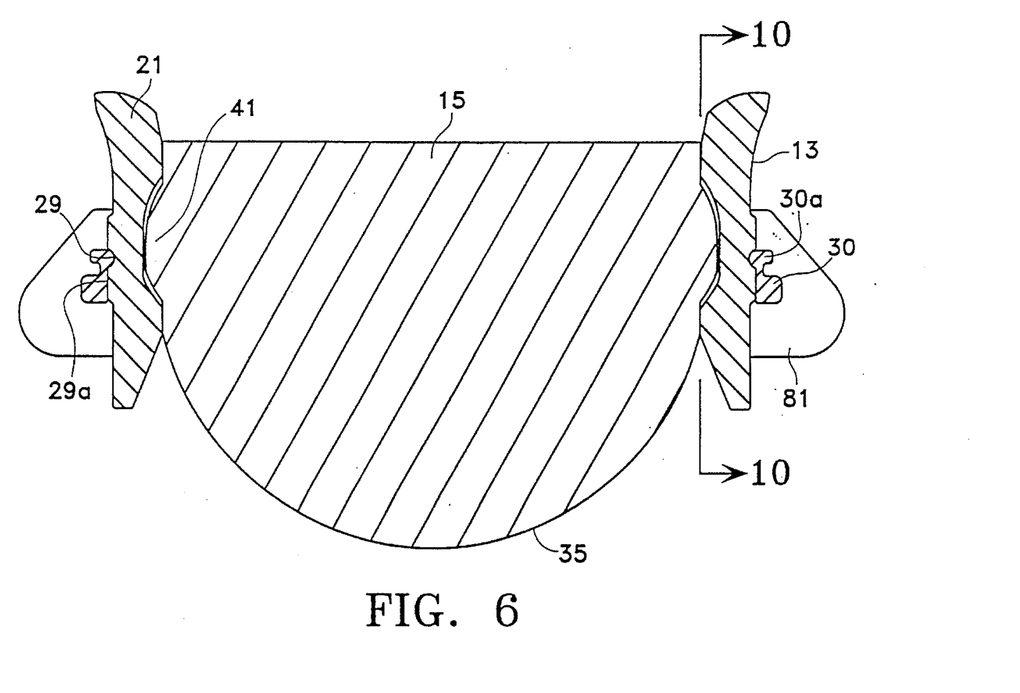
FIG. 6 is a vertical sectional view through the valve taken generally along the line 6—6 of FIG. 2 with the leaflet in the full open position.

The irregular ring 30 is shaped so that a section having an inwardly arcuate cross section is received in the arcuate cross section groove and the adjacent section having an inwardly cylindrical surface is seated snugly upon one of the two raised bands 29a that flank the groove 29, depending upon whether a mitral or an aortic sewing ring is to be installed. The unique stiffening ring 30 is designed to facilitate the installation of either an aortic sewing ring or a mitral sewing ring exterior of the valve body 13, as best seen by comparing FIGS. 2 and 2A. In FIG. 2, an aortic sewing ring 81 is illustrated which is designed to leave the upstream exterior surface of the valve body free and clear to permit its insertion into the aortic annulus from which the defective natural valve was excised. For this installation, the irregular stiffening ring 30 is slid onto the valve body 13 from the downstream end with the smaller section having the arcuate, radially inward projections leading. Each of the projections are connected by a thin neck section to the main portion of the stiffening ring as best seen in FIGS. 3 and 3A, which has a cylindrical radially interior face. When the leading projections reach the downstream band 29a flanking the groove 29, sufficient deflection occurs for the ring to continue its upstream travel until the groove is reached, into which the projections then snap in place, as seen in FIG. 6, with the main portion of the stiffening ring tightly surrounding the downstream cylindrical band 29a of the valve body and preferably placing it in at least slight compression.

Figure 2A:
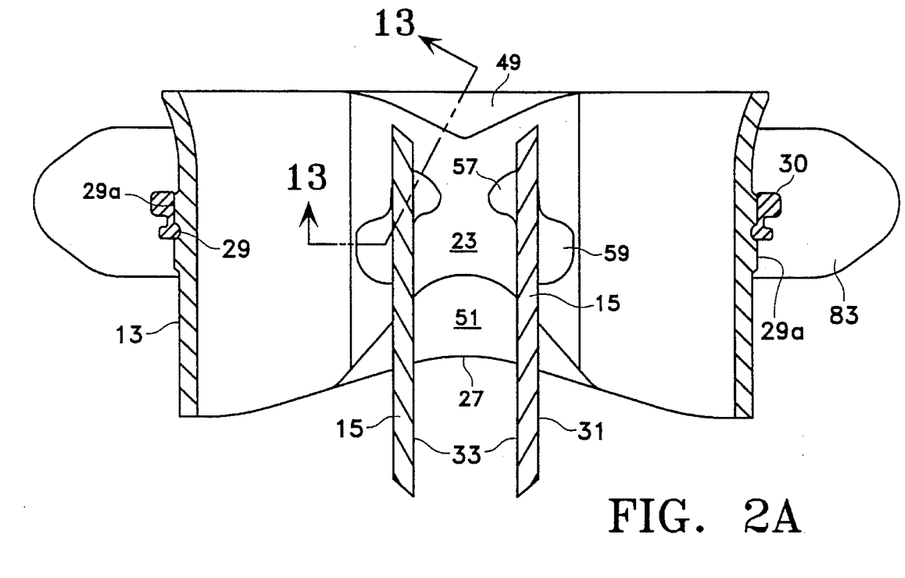
FIG. 2A is a sectional view taken generally along the line 2—2 of FIG. 1 showing the leaflets in the full open position, and with an alternative suture ring attached to the valve body.
Figure 3:
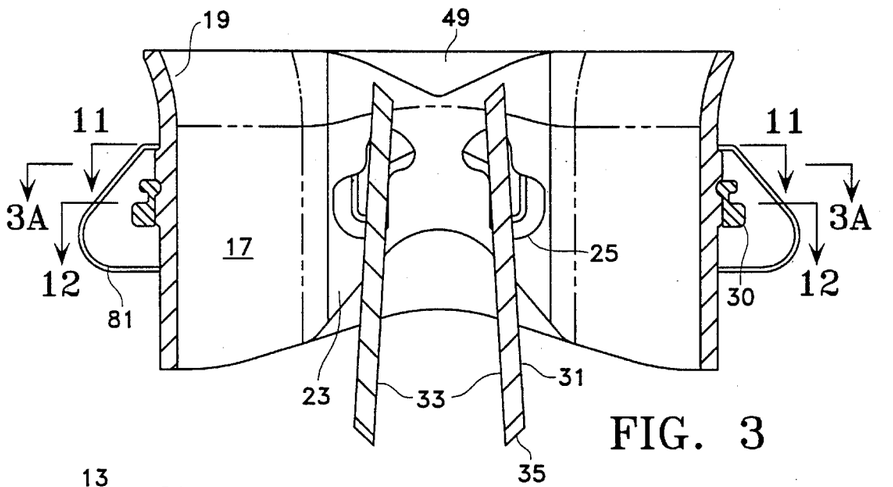
FIG. 3 is a view similar to FIG. 2 showing the leaflets in their prerotation orientation as they would be when the downstream flow of blood slows prior to reversal.
Figure 3A:
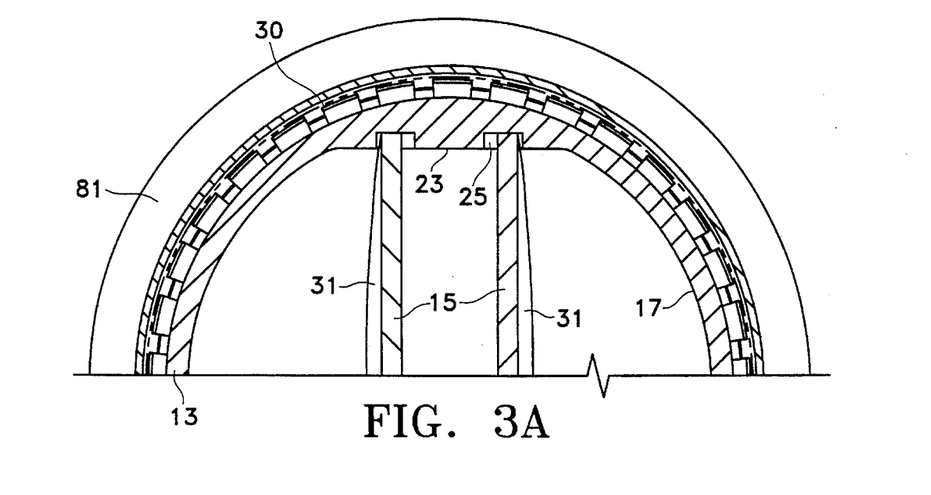
FIG. 3A is a fragmentary sectional view taken along the lines 3A—3A of FIG. 3.

When the valve body is to be equipped with a mitral sewing ring 83 as depicted in FIG. 2A, such sewing ring is positioned so as to occupy a major portion of the exterior wall surface of the valve body 13 upstream of the groove 29, leaving the downstream section free for insertion into the tissue annulus from which the defective natural valve was excised. For this sewing ring, the stiffening ring 30 is installed with the opposite orientation, being slid upward from the downstream end of the valve body 13 with the larger section of the ring 30 having the cylindrical radially interior surface leading. When it reaches the downstream band 29a, it can be forced upstream therepast, and the arcuate inward-facing surfaces of the projections again slide over the downstream band 29a as a result of the combined deflection which occurs. The projections again snap in place in the groove 29, but in this instance the major section of the ring 30 is seated tightly about the upstream band 29a, as shown in FIG. 2A.

Figure 5:
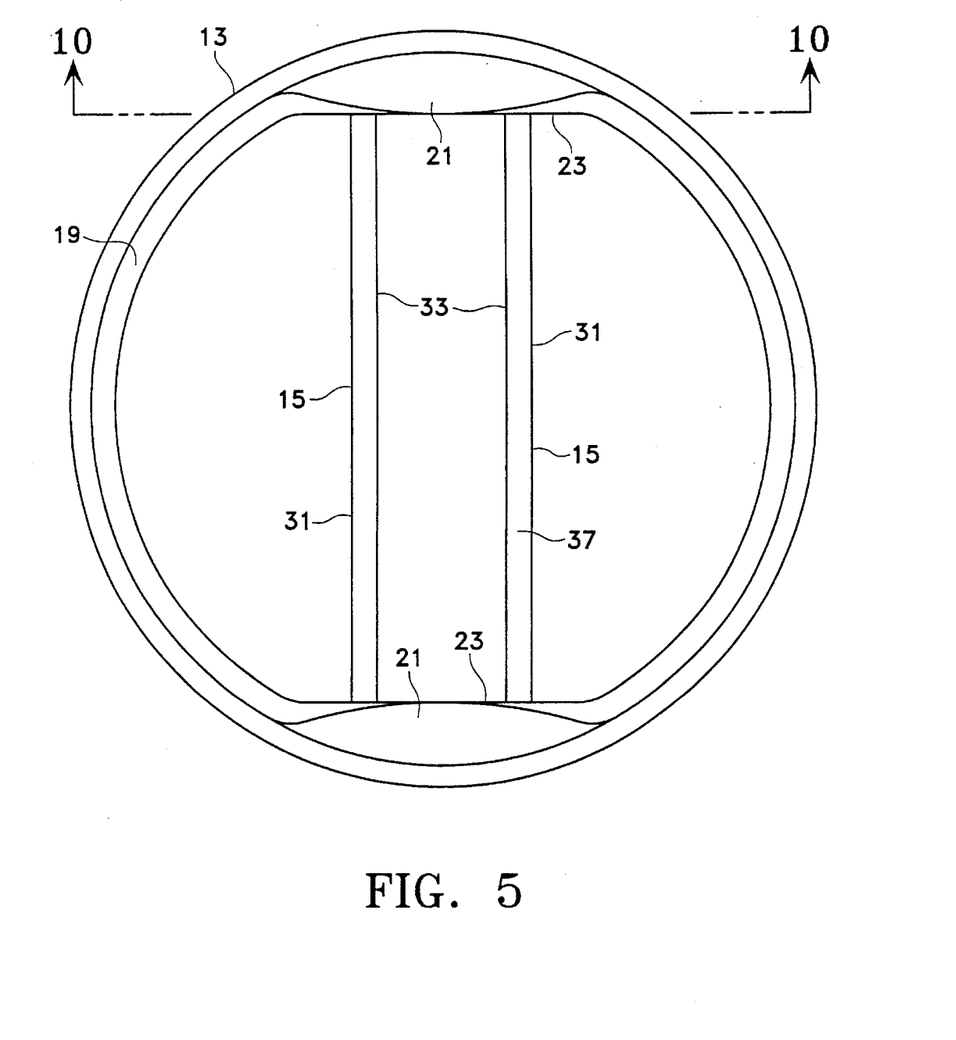
FIG. 5 is a plan view looking downward at the valve shown in FIGS. 1 and 2 with the leaflets in the full open position.

With the heart valve operatively installed in a patient, when it is in the open position, the two leaflets 15 assume an open equilibrium position with respect to the high flow and the direction of blood downstream through the passageway, which may be an orientation where they are precisely parallel to the centerline plane, as illustrated in FIGS. 2 and 2A. The location of the ear 41 within the cavity is illustrated in FIG. 10, from which it should be apparent that, should the dynamic blood forces within the valve body passageway change, the lefthand leaflet which is shown can rotate slightly clockwise so as to maintain such a low energy position either with or without some slight translation. In such an equilibrium position, the leaflets 15 provide very low obstruction to the downstream flow of blood. Yet, despite even such a precisely parallel, full open position, the pivot construction is such that any translational movement either downstream or upstream from this precisely parallel position causes the leaflets to rotate in the direction of closing. Furthermore, in the fully open position as shown in FIG. 2, the leaflets 15 are mounted so as to divide the valve body passageway into 3 sections, a center section located between the two leaflets 15 and two flanking sections. As best seen in FIG. 5, the arrangement is such that the cross-sectional area of each of the two flanking passageway sections is preferably at least as large as the cross-sectional area of the center flow passageway section.

Figure 10A:
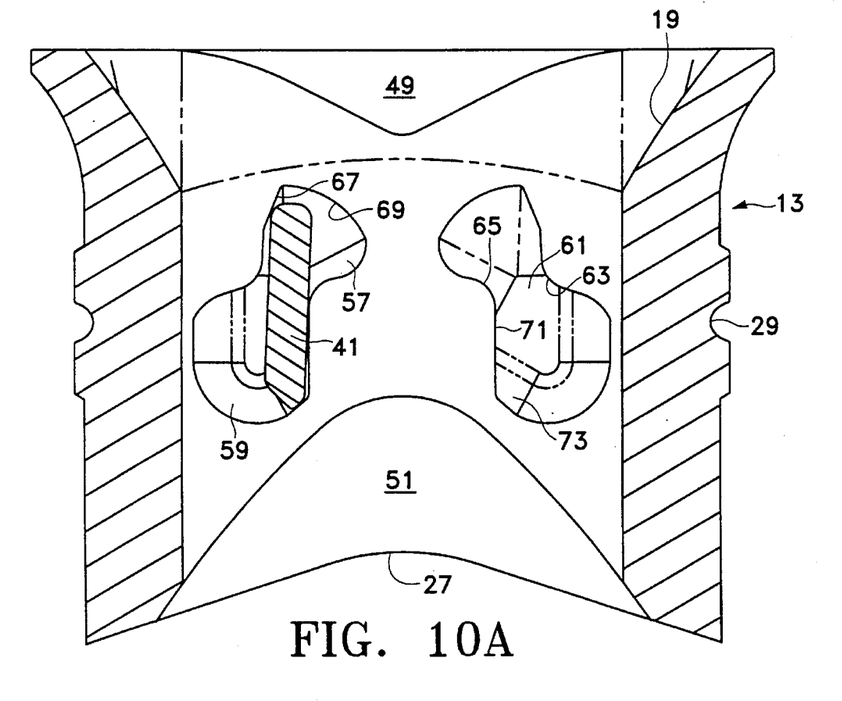
FIGS. 10A through 10D are full sectional views similar to FIG. 10 with the right-hand leaflet omitted and with the left-hand leaflet shown respectively (A) in the prerotation position, (B) at the beginning of closing movement, (C) in an intermediate position during closing movement and (D) at its full closed position.

During conditions of high rate of flow of blood downstream through the valve body, both leaflets 15 can be oriented precisely parallel to the centerline of the valve with the outflow surfaces of the ears 41 in contact with the flat wall sections 71 of the downstream lobes of the cavities 25 and with the ear upstream edge in juxtaposition with the camming wall 67 so that rotation past the parallel orientation is prohibited. The flow rate of blood through the valve during the pumping stroke of the associated chamber of the heart will generally exert sufficient force upon the inflow surfaces 31 of the leaflets such as to maintain the leaflets in this precisely parallel alignment. However, when the peak downstream flow of blood has passed so that it slows in its approach to zero flow, prior to the beginning of the reverse flow cycle, the forces of the flowing bloodstream tending to orient the leaflets in such a parallel position lessen, and as a result, the drag of the bloodstream against all of the surfaces of the leaflet becomes the predominant force. This net force tends to move the leaflets and the ears 41 slightly farther downstream, which is permitted by the contour of the downstream lobes 59. However, such further downstream leaflet movement is guided by the engagement of the outflow surface edges of the downstream ear surfaces 45 along the sloping sections 73 of the cavity and the inward fulcrums 65. The result of the ears 41 shifting to such downstream positions, as shown in FIG. 10A, is that the leaflets are no longer parallel to the centerline; instead, they have rotated slightly toward the closed orientation, i.e. so that they are now preferably at an angle to the centerline of about 2° to about 5°, and preferably 3° or greater, as depicted in FIG. 3. This prerotation of the leaflets 15 occurs near the end of pumping stroke and reduces the amount of regurgitation, i.e. the volume of blood which will pass upstream through such prosthetic heart valve prior to the occluders next reaching their fully closed position orientations, on the next closing. This reduction occurs for the following two reasons: (a) the leaflets now need to pivot a fewer number of angular degrees to reach the closed position by reason of the headstart they have from the precisely parallel orientation and (b) the backflowing blood has the immediate opportunity to preferentially contact the leaflet outflow surfaces 33, as opposed to the inflow surfaces 31, so that this component of the overall forces being applied to the leaflets during closing is increased.

Figure 10B:
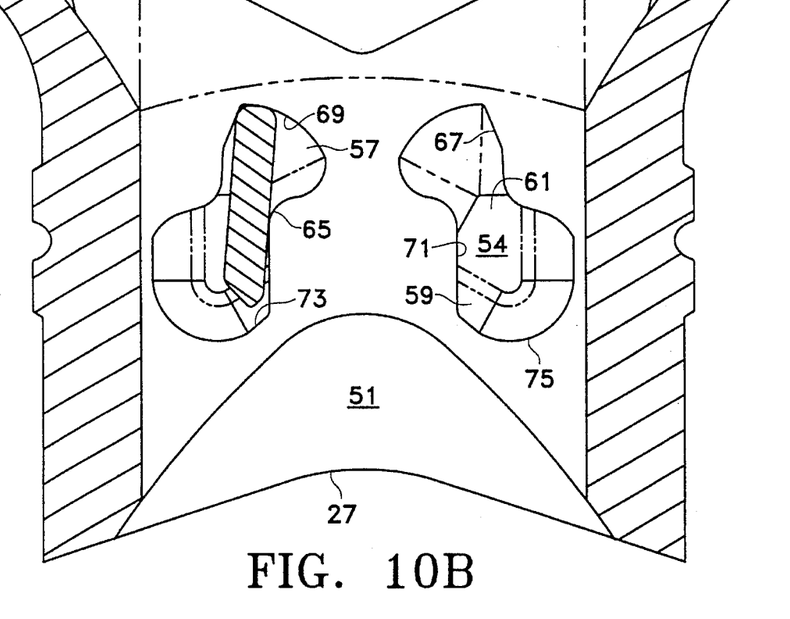

More specifically, as the reverse flow of blood upstream through the valve begins, the leaflets 15 and the ears 41 immediately translate upstream. This upstream translation of the ears causes immediate camming engagement of the inflow surface edge of each upstream edge surface 43 against the adjacent straight camming wall section 67 of each cavity, while the outflow surfaces of the ears may slide along the rounded inward fulcrums 65. By camming engagement is meant contact wherein there is relative sliding movement along a surface which is inclined to the direction in which the net forces are attempting to move an object, i.e. upstream and parallel to the centerline of the valve body; this camming action causes the leaflet to very promptly pivot toward its closed position while the translation movement continues. Accordingly, upstream translational movement of the ear in the cavity 25 assures that the pivoting of each leaflet toward its closed position orientation occurs promptly at the very beginning of reverse flow and continues, driven by these forces, until the upstream edges of the leaflet ears reach the top of the upstream lobes 57, as illustrated in FIG. 10B. Such initial pivoting is guided by the movement of the inflow surface edge of the ear upstream surface 43 along the camming surface 67 while the outflow ear surface generally slides along the inward fulcrum 65, causing such pivoting or rotation to take place about a center of rotation of pivot that is remote, i.e. which is located substantially past the centerline plane of the valve body; as a result, the length of the moment arm acts to accelerate the initial rotational closing movement. Very low friction is encountered because there is no engagement between the ears and the walls of the cavities such as would create a significant frictional force that would resist closing.

Figure 10C:
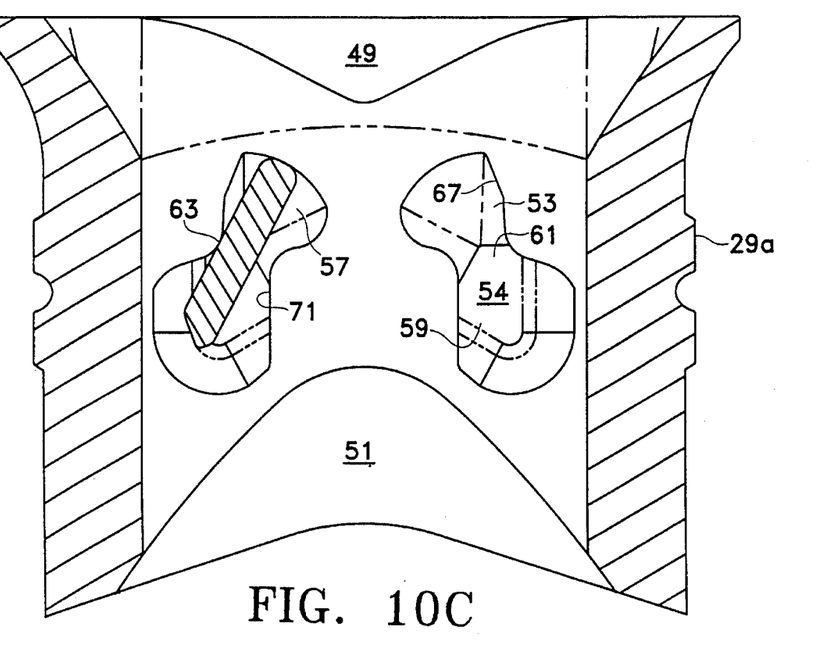
Figure 10D:
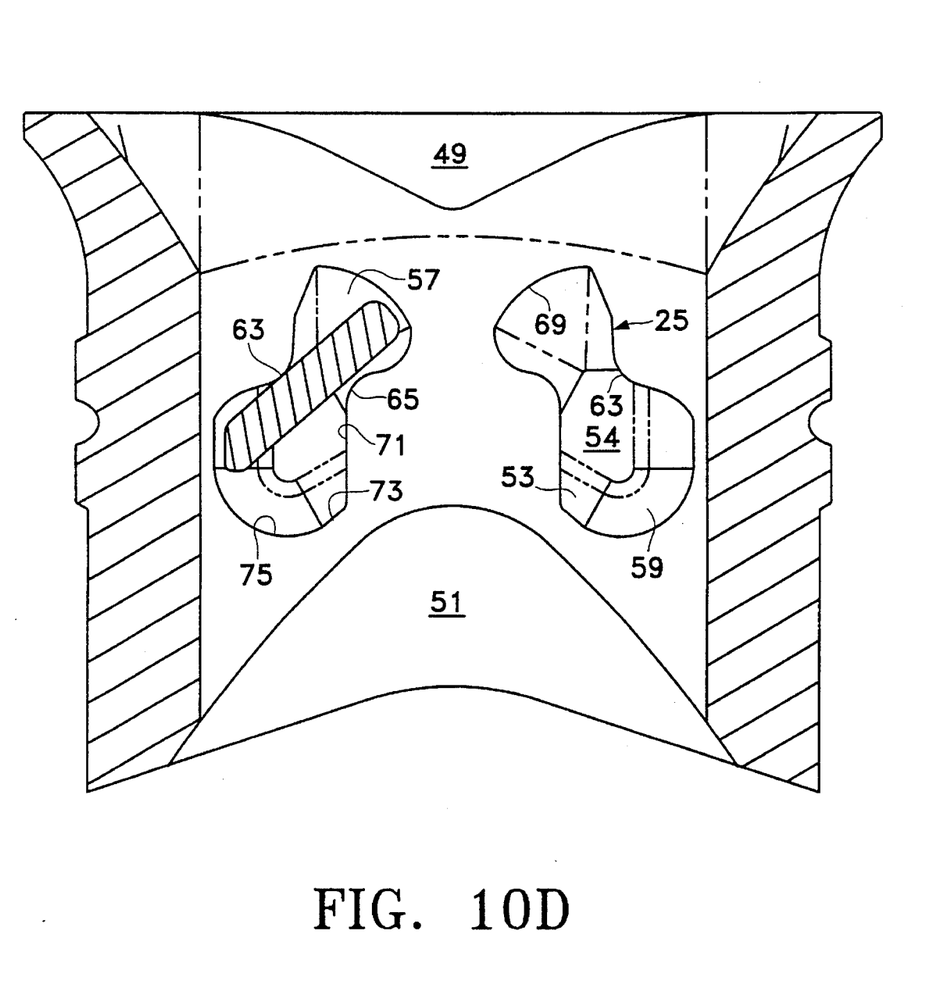
Figure 11:
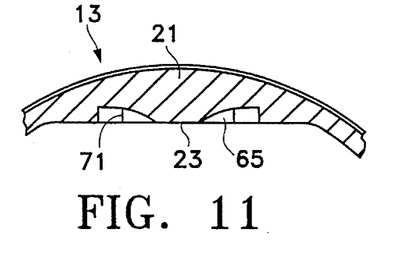
FIGS. 11 and 12 are fragmentary horizontal sectional views taken respectively along the lines 11—11 and 12—12 of FIG. 3, with the leaflets removed.

When the force of the backflowing blood against the outflow surface 33 of each leaflet has become significant, it causes the inflow surfaces of the ears to contact the outward fulcrums 63, as shown in FIG. 10C, and pivoting thereafter continues guided in part by sliding contact with the outward fulcrum 63. The leaflet has thus pivoted a significant amount as a result of the upstream translation and the shifting to contact with the outward fulcrum 63. Thereafter, the upstream edge surfaces of the ears are guided by movement along the arcuate wall section 69 while the ears simultaneously engage the outward fulcrums 63. Contact with the concave wall sections 69 and the fulcrums 63 remains substantially continuous, and the wall 69 is designed so that substantially only rotational motion occurs as the leaflets thereafter travel to the fully-closed position, as illustrated in FIG. 10D and in FIG. 4. In such position, mating edge surfaces 37 of the leaflets abut each other, and the downstream arcuate edge surfaces 35 of the leaflets abut and seat against the cylindrical interior surface 17 of the valve body. During a major portion of the closing movement and specifically during the final stages, this motion is almost pure rotational motion to avoid sliding of the ears along the fulcrums at this time when the upstream edges of the ears move slightly downstream as a result of this rotation. When the mating edges 37 of the two leaflets meet, the contact between the upstream edge of each ear and the arcuate wall 69 is broken, as seen in FIG. 10D, thus avoiding the possibility of localized wear when the pressure across the valve is very high. When the leaflet reaches its nearly closed position, the liquid between the edge 35 of the leaflet and the orifice wall acts like a cushion, and the leaflet further decelerates just before it impacts the wall, reducing the noise and any propensity for cavitation.

In the fully closed valve with the leaflets 15 oriented as illustrated in FIG. 4 wherein they are shown in elevation, the force of the blood against the outflow surface 33 of each leaflet is borne mainly by the downstream arcuate edge surfaces 35 seating against the interior valve body surface and by the ears 41 bearing against the outward fulcrums 63. At the instant complete closure is achieved, the pressure of the blood against the outflow surfaces of the leaflets is at its highest and results in controlled leakage through the cavities 25 in an upstream direction. Such leakage is around and past the ears 41 in each cavity as can be seen from FIG. 10D and is controlled in part by the depth and the length of the ears 41. The dimensioning of the ears and the cavities creates a pathway for controlled backflow past the lateral edges of the leaflet ears and thus tends to concentrate such leakage backflow in the regions of the pivot arrangements where such cleansing flow serves to positively guard against the occurrence of clotting. In this respect, the average clearance between the lateral edges of the ears 41 and the walls of the cavities 25 is preferably at least about 50 microns or about 0.002 inch, with the clearance being the least at the region of the apex of the curved upstream edge surface 43. There may be slightly greater clearance adjacent the edge surfaces 45 (FIG. 7) of the ears because of the translating design of the leaflets.

When blood flow again reverses, as for example when the pumping stroke of the associated chamber begins again, downstream displacement, i.e. translation, of the leaflets 15 initially occurs as a result of the force of the blood against the inflow surfaces 31. As is evident from FIG. 10D, the outflow surfaces of the ears 41 will quickly come in contact with the inward fulcrums 65, causing opening pivoting motion to quickly begin. The downstream edge surfaces 45 of the ears will likely reach the lower arcuate ends 75 of the downstream lobes 59 prior to the ears rotating completely about their pivot points on the fulcrums 65; however, when the blood flow through the valve approaches maximum, the net forces on the inflow surfaces 31 of the leaflets are such that the ears will be ramped upstream along the sloping wall sections 73, causing the leaflets to be displaced just slightly upstream until the precisely parallel position shown in FIG. 10 is reached, with the ears abutting the flat wall section 71 in each downstream lobe.

By confining substantially all of the functionally engaging surfaces that define the paths of opening and closing movement of the leaflets to the regions of the cavities and the ears, many of the regions where it is necessary to hold very close tolerance are concentrated, thereby facilitating both manufacturing processes and quality-control fitting-up procedures. By a design which limits the final closing movement of the leaflets to one of substantially only rotation, the likelihood of severe wear occurring at this point, when force on the leaflet ears is at about its maximum, is greatly diminished. These advantageous results are felt to grow out of this upstream-downstream lobe design where they are separated by a narrow throat 61, formed by the flanking fulcrums 63, 65 which confine the leaflet and assure smooth movement and positive resistance to jamming. The overall design is also such that the gross hemodynamics in terms of energy loss per cardiac cycle are completely acceptable.

Because blood is a very delicate tissue and even minor abuses caused by turbulence and high shear can result in thrombosis or emboli generation at local regions of stagnation, it is very important that excessive turbulence coupled with high shear stresses and local regions of stasis be avoided. The foregoing valve design has been found to excellently fulfill such requirements. The employment of leaflets with rectilinear surfaces that are free to follow and orient themselves even precisely parallel to straight downstream blood flow minimizes the turbulence associated with the leaflets themselves. The overall design of the cavities also effects prerotation of the leaflets after the downstream flow through the valve has peaked and nears the end of its cycle. This fact, in combination with the pivot arrangement itself and the location of the side notches 27 in the valve body that focus the inflowing blood against the outflow surfaces 33 where the initial closing rotation forces are amplified, all contribute to reducing regurgitation without increasing turbulence.

Although the invention has been described with respect to certain preferred embodiments, which include what the inventors presently consider to be the best mode for carrying out the invention, it should be understood that various changes and modifications that would be obvious to one having the ordinary skill in this art may be made without departing from the scope of the invention which is defined by the claims appended hereto. For example, as earlier indicated, the invention is not limited to occluders in the form of leaflets having flat body sections but is considered to be also applicable to leaflets having curved body sections. In this respect, it may be desirable to facilitate the creation of a central passageway of greater area through such a bileaflet valve by employing a pair of curved leaflets to achieve a different distribution of the downstream blood flow through the valve body.

Particular features of the invention are emphasized in the claims which follow.

What is claimed:

1. A prosthetic heart valve including
   a generally annular valve body having an interior, generally arcuate wall surface which defines a central passageway for blood flow therethrough which is generally symmetrical about a longitudinal centerline,
   a pair of cooperating leaflets, each having an inflow surface and an outflow surface, said leaflets being mounted in said valve body to alternate between an open position where the flow of blood in a downstream direction is permitted and a closed position where the flow of blood in the reverse direction is blocked, and
   a pivot arrangement by which said leaflets are guided in moving between said open and closed positions,
   said pivot arrangement permitting said pair of leaflets to assume an orientation substantially parallel to said longitudinal axis in a full open position at a high rate of downstream flow of blood,
   said pivot arrangement comprising two ears respectively projecting laterally from opposite side edges of each said leaflet and two pairs of diametrically opposed cavities in said interior surface of said valve body for receiving said ears,
   said ears each being elongated in an upstream-downstream direction when said leaflets are in the open position so as to have an upstream lateral edge surface and a downstream lateral edge surface,
   said leaflets being axially displaceable upstream, relative to said valve body, upon the reversal of blood flow, and
   said cavities each being formed with an upstream lobe and a downstream lobe which are separated by a throat section defined by convex outward and inward fulcrums, said upstream lobe having formed therein a straight camming wall oriented at an angle of between about 5° and about 30° to a plane containing said centerline and said downstream lobe having formed therein a flat wall section substantially parallel to said centerline so that, upon upstream axial displacement of said leaflets, a camming action is exerted upon said upstream lateral edge surface of each of said leaflet ears as a result of its engagement with said camming walls in said cavities, which camming action is effective to cause each said leaflet to immediately begin to swing toward its closed position orientation.

2. A prosthetic heart valve according to claim 1 wherein each said ear has substantially flat outflow and inflow surfaces which are parallel to each other.

3. A prosthetic heart valve according to claim 2 wherein each said cavity has said outward fulcrum formed therein at a location downstream of said straight camming wall so that said inflow surface of said ear slides against said fulcrum as said leaflet pivots to the closed position.

4. A prosthetic heart valve according to claim 3 wherein said upstream lobe of each said cavity includes a concave arcuate wall extending generally in a downstream direction from an upstream end of said straight camming wall, against which arcuate wall said upstream lateral edge surface of said ear slides when said leaflet continues to pivot to the closed position.

5. A prosthetic heart valve according to claim 4 wherein straight flat camming wall and said arcuate wall are located in said upstream lobe so that said upstream edge of said ear moves continuously downstream during the final portion of closing movement of the leaflet which is one of substantially only rotation.

6. A prosthetic heart valve according to claim 5 wherein said leaflets have substantially rectilinear outflow and inflow surfaces.

7. A prosthetic heart valve according to claim 6 wherein said rectilinear outflow and inflow surfaces are flat and parallel to each other.

8. A prosthetic heart valve according to claim 7 wherein said leaflet ears have inflow and outflow surfaces which are substantially coplanar with said inflow and outflow surfaces of said leaflets, and wherein said flat wall in said downstream lobe provides a locator surface against which said outflow surface of said ear may abut in the full open position.

9. A prosthetic heart valve according to claim 8 wherein each said cavity includes a downwardly sloping surface that extends downstream from the downstream end of said flat locator wall, which sloping surface has sufficient length that when downstream blood flow through the valve body slows prior to reversal, said leaflet is caused to rotate at least 3° toward its closed position as a result of a downstream edge of said ear outflow surface sliding along said sloping surface.

10. A prosthetic heart valve according to claim 9 wherein said inward fulcrum is located at the upstream end of said flat locator wall and wherein the dimension of said throat section is such that said outflow surface of said ear is in contact with said inward fulcrum during at least initial opening movement of said leaflet.

11. A prosthetic heart valve according to claim 10 wherein said ear upstream edge surface is rectilinear and substantially perpendicular to said flat outflow and inflow surfaces of said leaflet.

12. A prosthetic heart valve according to claim 11 wherein said valve body has an interior surface comprising sections of a right circular cylinder and wherein each said leaflet has a minor mating flat edge surface which abuts the mating edge of the other leaflet in the closed position and has a major arcuate edge surface which abuts said interior cylindrical wall surface of said valve body in the closed position, said minor mating edges being located at the upstream edge of each leaflet in the open position.

13. A prosthetic heart valve including a generally annular valve body having an interior, generally arcuate wall surface which defines a central passageway for blood flow therethrough, which is generally symmetrical about a longitudinal centerline and which includes two diametrically opposed flat wall sections, a pair of cooperating leaflets, each having an inflow surface and an outflow surface, said leaflets being mounted in said valve body to alternate between an open position where the flow of blood in a downstream direction is permitted and a closed position where the flow of blood in the reverse direction is blocked, and a pivot arrangement which guides said leaflets in moving between said open and closed positions and permits said pair of leaflets to assume an orientation substantially parallel to said longitudinal centerline in a full open position at a high rate of downstream flow of blood, said pivot arrangement comprising two ears respectively projecting laterally from opposite side edges of each said leaflet and two pairs of diametrically opposed cavities in said interior surface of said valve body for receiving said ears, two of said cavities being located in each said flat wall section, said ears being elongated in an upstream-downstream direction when said leaflets are in the open position and each having an upstream lateral edge surface and a downstream lateral edge surface, said leaflets and said ears being axially displaceable upstream, relative to said valve body, upon the reversal of blood flow, as permitted by movement of said ears within said cavities, said cavities each being formed with an upstream lobe and a downstream lobe which lobes are separated by a throat section defined by convex outward and inward fulcrums which are spaced apart a sufficient distance so that said ear is accommodated therebetween, said upstream lobe having formed therein a straight camming wall oriented at an angle of between about 5° and about 30° to a plane containing said centerline and said downstream lobe having formed therein a flat wall section substantially parallel to said centerline, and said cavities being proportioned relative to said ears so that said ears are always disposed in said throat section whereby said ear lies in juxtaposition to said flat wall section of said downstream lobe in said open position, and whereby, upon upstream axial displacement of said leaflets, a camming action is exerted upon said upstream lateral edge surface of each of said leaflet ears as a result of its engagement with said straight camming walls in said cavities, which camming action is effective to cause each said leaflet to immediately begin to swing toward its closed position orientation.

14. A prosthetic heart valve according to claim 13 wherein each said ear has substantially flat outflow and inflow surfaces which are parallel to each other.

15. A prosthetic heart valve according to claim 14 wherein said upstream lobe of each said cavity includes a concave arcuate wall extending generally downstream from an upstream end of said straight camming wall, against which arcuate wall said upstream lateral edge surface of said ear slides when said leaflet continues to pivot to the closed position.

16. A prosthetic heart valve according to claim 15 wherein each said cavity has said outward fulcrum formed therein at a location downstream of said straight camming wall so that said inflow surface of said ear contacts said fulcrum as said leaflet pivots to the closed position with said ear moving along said concave arcuate wall.

17. A prosthetic heart valve according to claim 16 wherein said straight camming wall and said arcuate wall are located in said upstream lobe so that said upstream lateral edge surface of said ear moves continuously downstream during the final portion of closing movement of the leaflet which is one of substantially only rotation.

18. A prosthetic heart valve according to claim 13 wherein said straight camming wall is oriented at an angle of between about 15° and about 25° to said centerline plane.

19. A prosthetic heart valve including a generally annular valve body having an interior, generally arcuate wall surface which defines a central passageway for blood flow therethrough, which is generally symmetrical about a longitudinal centerline and which includes two diametrically opposed flat wall sections and surfaces which are sections of a right circular cylinder, a pair of cooperating leaflets, each having a flat inflow surface, a flat outflow surface, a minor mating flat edge and a major arcuate edge surface, said leaflets being mounted in said valve body to alternate between an open position where the flow of blood in a downstream direction is permitted and a closed position where the flow of blood in the reverse direction is blocked and said leaflet minor edges abut each other and said major edges abut said interior right circular cylindrical wall surface sections of said valve body, said minor mating edges being located at the upstream edge of each leaflet in the open position, and a pivot arrangement which guides said leaflets in moving between said open and closed positions and permits said pair of leaflets to assume an orientation substantially parallel to said longitudinal centerline in a full open position at a high rate of downstream flow of blood and to rotate at least about 3° toward the closed position as the downstream flow of blood slows prior to reversal, said pivot arrangement comprising two flat ears respectively projecting laterally from opposite side edges of each said leaflet and two pairs of diametrically opposed cavities in said interior flat wall sections of said valve body for receiving said ears, two of said cavities being located in each said flat wall section, said flat ears being elongated in an upstream-downstream direction when said leaflets are in the open position and each having an upstream lateral edge surface and a downstream lateral edge surface, said leaflets and said ears being axially displaceable upstream, relative to said valve body, upon the reversal of blood flow, as permitted by movement of said ears within said cavities, said cavities each being formed with an upstream lobe and a downstream lobe which lobes are separated by a throat section defined by convex outward and inward fulcrums which are spaced apart a sufficient distance so that said flat ear is accommodated therebetween, said upstream lobe having formed therein a straight camming wall oriented at an angle of between about 5° and about 30° to a plane containing said centerline and said downstream lobe having formed therein a flat locator wall section substantially parallel to said centerline which extends downstream from said inward fulcrum, and said upstream lobe also includes a concave arcuate wall extending generally downstream from an upstream end of said flat camming wall against which arcuate wall said upstream lateral edge surface of said ear slides when said leaflet continues to pivot to the closed position, each said cavity also includes a downwardly sloping surface in said downstream lobe that extends downstream from the downstream end of said flat locator wall, said cavities being proportioned relative to said ears so that said ears are always disposed in said throat section whereby said flat ear lies in juxtaposition to said flat locator wall section of said downstream lobe in said open position until blood flow slows when a downstream edge of said outflow surface of said ear slides along said sloping surface when downstream blood flow through the valve body slows prior to reversal so that said leaflet is caused to rotate at least 3° toward its closed position, whereby, upon upstream axial displacement of said leaflets, a camming action is exerted upon said upstream lateral edge surface of each of said leaflet ears as a result of its engagement with said straight camming walls in said cavities, which camming action is effective to cause each said leaflet to immediately begin to swing toward its closed position orientation.

* * * * *